United States Patent
Tao

(10) Patent No.: US 7,176,260 B2
(45) Date of Patent: Feb. 13, 2007

(54) SOFT NITRILE MEDICAL GLOVES HAVING IMPROVED GLOVE RELAXATION PROPERTIES

(75) Inventor: Jian Tao, Reno, NV (US)

(73) Assignee: Microflex Corporation, Reno, NV (US)

( * ) Notice: Subject to any disclaimer, the term of this patent is extended or adjusted under 35 U.S.C. 154(b) by 0 days.

(21) Appl. No.: 10/755,676

(22) Filed: Jan. 13, 2004

(65) Prior Publication Data

US 2004/0176512 A1 Sep. 9, 2004

Related U.S. Application Data

(63) Continuation-in-part of application No. 10/120,796, filed on Apr. 12, 2002, now abandoned, and a continuation-in-part of application No. 09/877,034, filed on Jun. 11, 2001, now Pat. No. 6,451,893.

(51) Int. Cl.
*C08F 236/12* (2006.01)
*C08F 36/06* (2006.01)

(52) U.S. Cl. .............. 525/329.3; 525/329.1; 525/332.6; 524/432; 524/413; 524/565; 524/566; 524/571; 524/201; 524/87; 524/95; 524/106; 524/82; 524/83; 524/84; 2/168

(58) Field of Classification Search ............ 524/432, 524/567, 394, 413, 565, 566, 571; 525/332.6; 525/329.3, 329.1; 2/168
See application file for complete search history.

(56) References Cited

U.S. PATENT DOCUMENTS

| | | |
|---|---|---|
| 5,014,362 A | 5/1991 | Tillotson et al. ............. 2/168 |
| RE35,616 E | 9/1997 | Tillotson et al. |
| 5,872,173 A | 2/1999 | Anand ...................... 524/494 |
| 5,881,387 A | 3/1999 | Merovitz et al. ............ 2/161.7 |
| 6,000,061 A | 12/1999 | Taneja et al. ................ 2/168 |
| 6,013,727 A | 1/2000 | Dharmarajan et al. ........ 525/72 |
| 6,031,042 A | 2/2000 | Lipinski .................... 524/566 |
| 6,673,404 B1 * | 1/2004 | Yeh et al. ................. 428/35.7 |
| 2002/0193488 A1 * | 12/2002 | Tao ......................... 524/418 |

FOREIGN PATENT DOCUMENTS

| | | | |
|---|---|---|---|
| JP | 2000-96321 A | * | 4/2000 |
| WO | WO 00/21451 A1 | * | 4/2000 |

OTHER PUBLICATIONS

JP 2000-96321 (abstract in English).*

* cited by examiner

*Primary Examiner*—Ling-Sui Choi
*Assistant Examiner*—Rip A. Lee
(74) *Attorney, Agent, or Firm*—Evan M. Kent; Stewart L. Gitler

(57) ABSTRACT

The invention is the manipulation of the zinc oxide content and sulfur content of nitrile butadiene rubbers and selected vulcanization conditions that can be achieved economically with common production facilities. The manipulation of these components affects the relaxation property of gloves formed by this material. Produced are gloves that have a relaxation property, higher than 50%, and a low modulus (approximately 3 Mpa). The glove maintains decent ultimate tensile strength (>20 Mpa) and elongation (>500%). The glove is produced by a vulcanization process, which lasts from 5 to 60 minutes at temperatures ranging from 300° F. to 400° F. The tensile strength and elongation are well above the ASTM requirements for medical gloves. The current ASTM requirements are ASTM D412-92. Thanks to sufficient vulcanization, the films produced provide satisfactory protection from viral penetration. The tearing strength is also better because of the lower modulus.

3 Claims, No Drawings

SOFT NITRILE MEDICAL GLOVES HAVING IMPROVED GLOVE RELAXATION PROPERTIES

This application is a continuation-in-part of Ser. No. 09/877,034, filed Jun. 11, 2001 now abandoned and Ser. No. 10/120,796, filed Apr. 12, 2002 now U.S. Pat. No. 6,451,893.

BACKGROUND OF THE INVENTION

Natural rubber latex gloves provide excellent protection from numerous dangerous pathogens as well as many harsh chemicals. The natural rubber latex glove manufacturing industry mushroomed in early 1980s, especially in the Far East. However, soon after that, it was recognized that the inherent proteins of natural rubber latex would cause allergic reactions (Type I) to occur in certain people. In rare cases, the allergic reaction could be fatal. Therefore, for those people, alternatives, to natural rubber latex gloves, must be provided.

Although a series of synthetic materials including nitrile butadiene rubber (NBR), polychloroprene (CR), polyurethane (PU), polyisoprene (IR), polyvinyl chloride (vinyl, PVC), polyethylene (PE), etc. as well as many of their blends and copolymers have been used as alternatives to natural rubber latex, the overall performance and the cost of the alternatives are not quite satisfactory. Among the alternatives, nitrile butadiene rubber is the most popular one, an elastic glove at a reasonable cost.

U.S. Pat. No 5,014,312, and Reissue Patent RE 35,616, both issued to Tillotson et al, cover nitrile butadiene rubber gloves. The patents address relaxation properties. The stress (or modulus) of the material under constant strain at six minutes should be less than 50% of its initial value. Most of the nitrile gloves currently commercially available have their relaxation property clustered about 40%, although that could be varying from 30~45%. Other gloves might have improved tensile strength, or elongation, or fewer additives that could cause Type IV allergic reactions (ZnO, etc.). None of them have displayed relaxations at six minutes that could exceed 50%.

Tillotson et al compared relaxation properties between natural rubber latex and nitrile films, but has not shown that the relaxation property of nitrile films can be tuned within a certain range via proper formulation.

U.S. Pat. No. 6,031,042 issued to Lipinski reveals a nitrile rubber formulation. The formulation contains no zinc oxide and only 1.0 PHR sulfur resulting in a relaxation property of only approximately 40%. No consideration of adjusting the formulation to tune the relaxation property of the glove is contemplated.

U.S. Pat. No. 6,566,435 issued to Teoh et al discloses a nitrile latex formulation containing less than 0.5 PHR zinc oxide and sulfur. No contemplation is given to a product with a zinc oxide content of greater than 0.5 parts per hundred and less than 1.0 parts per hundred with a relation property tuned to above 50%. More over, the proposed formula restricted the latex to be used. It must consist of a carboxylated content between 2~6%. We found the content of the carboxylated group is not as critical as they claimed. Conversely, we used a product that contains 7% of carboxylated group and the relaxation property can still be much higher than 50%. We also tested the sample formula in this patent to make some films. The films do not age well.

Relaxation property is not an ASTM required quality control parameter for gloves. But together with modulus, another non-ASTM required quality control parameter for gloves; they can characterize the performance and the tactile sensation of a glove. The higher the relaxation property, the better the glove will fit a hand's shape. Otherwise, the glove becomes loose after a while. But if high relaxation were combined with high modulus, the glove would quickly cause finger fatigue. Natural rubber latex gloves has a (relaxation >80%, and a 300% modulus (<2 MPa), while nitrile butadiene rubber gloves show lower relaxation (typical 40%) and a much higher modulus at 300% (>7 Mpa).

Relaxation property is an intrinsic characteristic of material nature. Most nitrile butadiene latexes manufactured via emulsion polymerization would yield a relaxation of about 40%, as evidenced by the nitrile gloves currently available. This inherent property is predominantly caused by polymer chain structure, which would be determined by the polymerization mechanism. Different nitrile butadiene rubber vendors might have different controlling parameters and procedures, but their products have very little differentiation due to the fact that they all use emulsion polymerization for economic reasons.

Nitrile butadiene latexes, produced via polymerization mechanisms other than emulsification, namely for dipping applications could have quite different structure, and thus different relaxation profiles, but there are no such products that are commercially available right now because of cost. Once the polymer chain structure has been predefined in the polymerization, there is little one can do to manipulate it. It is an objective of the invention to tune this parameter (relaxation) to above 50%. Meanwhile, the other mechanical properties must meet ASTM requirements.

To evaluate the performance of a nitrile glove, relaxation is only one of many physical properties. Tensile strength, modulus, elongation, before and after aging, are all very important; as required by ASTM. Gloves depending on the designed application can emphasize different characteristics.

Three components in formulation are critical to affect these desired properties. First of all, sulfur is the crosslinker. Secondly, zinc oxide is the so-called primary activator for sulfur vulcanization. Lastly, the so-called secondary accelerators include zinc dibutyldithiocarbamate (ZDBC or BZ), zinc diethyldithiocarbamate (ZDEC or EZ), zinc 2-mercaptobenzothiazole (ZMBT), etc.

Through experimentation, we find out that ionic crosslinking will lead to strong tensile strength and good aging resistance, as desired. However, it also results in low elongation, high modulus, and low relaxation, as undesired. Zinc oxide free would result in highest relaxation, lowest modulus, and longest elongation. But the films don't age well. The films show fairly poor aged elongation (<400%).

Sulfur content is critical to relaxation. We made two series of films with sulfur content 1 PHR and 3 PHR but changed the zinc oxide from 1 PHR to 0. The correlation is clear. At 1 PHR of sulfur, relaxation would go from 35% to 45% by decreasing zinc oxide from 1 PHR to 0. At 3 PHR of sulfur, relaxation would go from 45% to 55%.

Having reduced zinc oxide, usually one has to add some more secondary accelerators to compensate, so that sulfur vulcanization can occur timely as desired. However, excessive secondary accelerators not only cause concerns on Type IV allergy, but also accelerate aging of the products during storage.

Varying the ratio of these three components, one can have optimized formulations for different desired applications.

SUMMARY OF THE INVENTION

The invention is the manipulation of the zinc oxide content, greater than 0.5 PHR to less than 1.0 PHR, sulfur content, 2 PHR to 5 PHR, and secondary accelerators, 0.5 PHR ~2 PHR, of nitrile butadiene rubbers and selected vulcanization conditions that can be achieved economically with common production facilities. The manipulation of these components affects the relaxation property of gloves formed by this material. Produced are gloves that have a relaxation property, higher than 50%, and a low modulus (approximately 3 Mpa). The glove maintains decent ultimate tensile strength (>20 Mpa) and elongation (>500%). And the glove must age well, aged elongation >400% and aged tensile strength >20 MPa. The tensile strength and elongation are well above the ASTM requirements for medical gloves. The current ASTM requirements are ASTM D412-92. Thanks to sufficient vulcanization, the films produced provide satisfactory protection from viral penetration. The tearing strength is also better because of the lower modulus.

DETAILED DESCRIPTION OF THE INVENTION

Compounding:

Carboxylated nitrile butadiene rubber undergoes two kinds of crosslinking in normal formulation and vulcanization. The first one is where carboxylated acid groups are linked to each other via a reaction with zinc oxide at room temperature. This is the so-called ionic crosslinking. The second kind of crosslinking is where unsaturated butadiene blocks are crosslinked via a conventional sulfur system at elevated temperatures. This is also referred as covalent crosslinking. One of our preferred formulations, produce films whose properties are comparable to those of natural rubber latex (300% modulus <2 Mpa, tensile strength >20 Mpa, and simultaneously elongation >500%). But, the relaxation at six minutes cannot be higher than 45%. Therefore, zinc oxide was adjusted to prevent a performance reduction. The resulting formulation is tabulated as following:

| INGREDIENTS | PHR |
|---|---|
| Nitrile Butadiene Rubber | 100 |
| 2,2'-methylene-bis-(4-methyl-6-butylphenol) | 0.5 |
| Zinc Oxide | 0.85 |
| Zinc dibutyldithiocarbamate (BZ) + Zinc 2-mercaptobenzothiazole | 0.7 |
| Sulfur | 3.0 |
| Potassium hydroxide | 1.0 |
| Titanium dioxide | 0.5 |

Mechanical Properties:

It was found it is possible to keep relaxation >50% at even higher ZnO levels via choosing proper nitrile latex and varying production parameters. As anticipated, the higher ZnO level is, the lower the relaxation and the tougher the glove is. Nevertheless, we now think a further optimized formula ought to contain higher ZnO level to give longer shelf life of the gloves.

| Description | Relaxation (R) | Aged Elongation (%) |
|---|---|---|
| ZnO 0 | 66 | 434 |
| ZnO 0.5 | 62 | 470 |
| ZnO 0.7 | 58 | 493 |
| ZnO 0.85 | 53 | 515 |
| ZnO 1.0 | 48 | 520 |

The correlation between ZnO and relaxation and aged elongation was formulated. 3.0 PHR of sulfur was used in all these data presented.

As a result, we found zinc oxide formulations with percentages ranging from greater than 0.5% to 1.0%, and vulcanization conditions yield higher relaxation properties, greater than 50%, and an improved soft glove. Each formulation had a sulfur component of 3.0 PHR. This combination shows a more balanced performance, not only relaxation >50% but also an extraordinary aged elongation >500%.

The zinc oxide compound exhibited relaxation greater than 50%. Powdering and/or leaching had no significant impact on glove properties. The formulations produce improved compounds and optimized vulcanization conditions (temperature and duration). The new formulations and procedures are easily realized economically under common nitrile-glove production lines. Depending on the desired applications, both powdered and powder free gloves could be produced in the same formula.

In a formulation with zinc oxide and sulfur, two kinds of crosslinking mechanisms govern the carboxylated NBR vulcanization. At room temperature, zinc oxide reacts with carboxylated groups to form ionic crosslinking, resulting in low relaxation. On the other hand, sulfur crosslinking, especially multi-sulfur crosslinking between double bounds of polybutadiene chains results in high relaxation. Varying the ratio of these two components, one can tune the relaxation to a certain level. The previously disclosed zinc oxide embodiment achieved at relaxation as high as 62%, compared to 40% with a normal zinc oxide and sulfur formula. With limited zinc oxide content of greater than 0.5 parts zinc oxide per 100 parts NBR and less than 1.0 parts zinc oxide per 100 parts NBR and 3.0–5.0 parts of sulfur per 100 parts NBR, a relaxation greater than 50% can still be achieved. The affect of the varied ratio of the zinc oxide and sulfur is summarized on the following table:

| Zinc Oxide Parts Per 100 parts NBR | Sulfur Parts Per 100 parts NBR | Relaxation (%) |
|---|---|---|
| 1 | 3 | 48 |
| 0.85 | 3 | 53 |
| 0.70 | 3 | 58 |
| 0.5 | 3 | 62 |

As can be seen, lowering the amount of zinc oxide increases the relaxation property. These elastomers were made under the same vulcanization process disclosed above.

| Zinc Oxide Parts Per 100 parts NBR | Sulfur Parts Per 100 parts NBR | Relaxation (%) |
|---|---|---|
| 0 | 1 | 48 |
| 0 | 1.5 | 50 |
| 0 | 2 | 54 |
| 0 | 2.5 | 54 |
| 0 | 3 | 59 |
| 0 | 3.5 | 61 |
| 0 | 5 | 62 |

When the formula are free of zinc oxide, it seems relaxation almost increases linearly with sulfur content at the beginning. Then, it level off after sulfur reached 3 PHR. Therefore; we also collected data for the formula with zinc oxide.

| Zinc Oxide Parts Per 100 parts NBR | Sulfur Parts Per 100 parts NBR | Relaxation (%) |
|---|---|---|
| 0.5 | 1 | 48 |
| 0.5 | 2 | 55 |
| 0.5 | 3 | 60 |
| 0.5 | 5 | 64 |
| 1 | 5 | 51 |
| 1.5 | 5 | 41 |

Instead of reach a plateau after 3 PHR of sulfur, the relaxation seems to continue to increase. And relaxation 50% is achieved even when zinc oxide is 1 PHR. But the other properties are not so desirable any more. The elongation before aged is less than 500% and modulus is >8 MPA, very tough.

As aforementioned, the third component in the formula is the level of secondary accelerators. When zinc oxide, the primary activator of sulfur vulcanization, level is low, relatively higher secondary accelerators are needed. Otherwise, to ensure sufficient vulcanization requires substantial heat or prolong vulcanization duration. However, excessive accelerators also result in poor aging resistance.

| Accelerators | Relaxation (R) | Aged Elongation (%) |
|---|---|---|
| 1.0 | 56 | 450 |
| 1.5 | 61 | 407 |
| 2.0 | 64 | 377 |

The sulfur is 3 PHR and zinc oxide is 0.5 PHR for these three films. The aging was conducted at 100° C. for 22 hours, as ASTM specified.

Although under the same vulcanization conditions, more accelerators result in higher relaxation, which is also desired, the aged elongation is clearly changing to undesired direction.

As mentioned previously, relaxation is an intrinsic property of the polymer structure and in carboxylated NBR; the most predominant factor is the chain structure of polybutadiene. In commercially available carboxylated NBR synthesized via emulsion polymerization, the polybutadiene block consists of three types of double bonds: 1,2; cis 1,4; and trans 1,4. More cis 1,4 structure yields high relaxation. It is possible to synthesize polybutadiene with cis 1,4 dominant structures in an organic solvent. In this way, it is possible to achieve higher relaxation, > than 80%, with the normal formula. For an NBR, which is not carboxylated, there is no reaction between the zinc oxide and carboxylated groups and therefore, the content of zinc oxide may not matter. Natural rubber may have a relaxation property > than 80% with 1 PHR of zinc oxide.

While the invention has been described with respect to a preferred embodiment, variations, modifications would be apparent to one of ordinary skill in the art without departing from the spirit of the invention.

What is claimed is:

1. An elastomer formulation for a glove comprising:
    a nitrile butadiene rubber latex;
    Sulfur ranging from about 2 to about 5 parts per hundred parts of the nitrile butadiene rubber latex; and
    Zinc oxide, said zinc oxide, present in an amount greater than 0.5 parts per hundred and less than 1.0 parts per hundred parts nitrile butadiene rubber, wherein said elastomer has a relaxation property greater than 50%.

2. The elastomer formulation for a glove as claimed in claim 1, further comprising:
    a secondary accelerator ranging from 0.5 to about 2 parts per hundred parts of the nitrile butadiene rubber latex.

3. The elastomer formulation for a glove as claimed in claim 2, wherein the secondary accelerator is selected from the group consisting of: zinc dibutyldithiocarbamate; zinc diethyldithiocarbamate; and zinc 2-mercaptobenzothiazole.

* * * * *

UNITED STATES PATENT AND TRADEMARK OFFICE
CERTIFICATE OF CORRECTION

| | | |
|---|---|---|
| PATENT NO. | : 7,176,260 B2 | Page 1 of 1 |
| APPLICATION NO. | : 10/755676 | |
| DATED | : February 13, 2007 | |
| INVENTOR(S) | : Tao | |

It is certified that error appears in the above-identified patent and that said Letters Patent is hereby corrected as shown below:

Column 1, line 58 please delete the word "relation" and replace same with --relaxation--;

Column 2, line 7, after the words "latex gloves", kindly delete "has" and replace same with --have--; and Column 5, line 30, after "Instead of", kindly delete "reach", and replace same with --reaching--.

Signed and Sealed this

First Day of May, 2007

JON W. DUDAS
*Director of the United States Patent and Trademark Office*